United States Patent [19]
Martin

[11] Patent Number: 5,297,698
[45] Date of Patent: Mar. 29, 1994

[54] TWO-STAGE MIXING AND DISPENSING ASSEMBLY FOR PREPARATIONS SUCH AS DENTAL CEMENTS

[75] Inventor: Thomas W. Martin, St. Paul, Minn.

[73] Assignee: Minnesota Mining and Manufacturing Company, St. Paul, Minn.

[21] Appl. No.: 869,872

[22] Filed: Apr. 16, 1992

Related U.S. Application Data

[63] Continuation-in-part of Ser. No. 735,995, Jul. 25, 1991, abandoned.

[51] Int. Cl.$^5$ .............................................. B65D 35/28
[52] U.S. Cl. ...................... 222/95; 206/219; 206/222; 222/136; 222/145; 222/327; 222/386; 433/90
[58] Field of Search ............... 222/95, 136, 145, 327, 222/386; 206/219, 221; 215/DIG. 8; 433/90

[56] References Cited

U.S. PATENT DOCUMENTS

| | | | |
|---|---|---|---|
| 2,887,253 | 5/1959 | Biedenstein | 222/327 |
| 3,537,605 | 11/1970 | Solowey | 215/6 |
| 3,595,439 | 7/1971 | Newby | 222/80 |
| 3,684,136 | 8/1972 | Baumann | 222/386 |
| 3,724,077 | 4/1973 | Preston et al. | 32/60 |
| 3,739,947 | 6/1973 | Baumann et al. | 222/136 |
| 3,766,917 | 10/1973 | Wimmer | 128/218 M |
| 3,814,717 | 6/1974 | Wilson et al. | 260/29.6 M |
| 3,907,106 | 9/1975 | Purrmann et al. | 206/219 |
| 4,198,756 | 4/1980 | Dragan | 222/326 |
| 4,209,434 | 6/1980 | Wilson et al. | 260/29.6 H |
| 4,295,828 | 10/1981 | Rudler | 433/90 |
| 4,515,267 | 5/1985 | Welsh | 206/219 |
| 4,648,532 | 3/1987 | Green | 222/82 |
| 4,872,936 | 10/1989 | Englebrecht | 156/307.3 |
| 5,026,283 | 6/1991 | Osanai et al. | 433/90 |
| 5,061,179 | 10/1991 | Dragan | 433/90 |
| 5,083,921 | 1/1992 | Dragan | 433/90 |
| 5,100,320 | 3/1992 | Martin et al. | 433/90 |
| 5,122,057 | 6/1992 | Discko, Jr. | 433/90 |
| 5,125,836 | 6/1992 | Dragan et al. | 433/90 |
| 5,129,825 | 7/1992 | Discko, Jr. | 433/90 |
| 5,165,890 | 11/1992 | Discko, Jr. | 433/90 |
| 5,172,807 | 12/1992 | Dragan et al. | 222/136 X |

FOREIGN PATENT DOCUMENTS

| | | |
|---|---|---|
| 0323120 | 7/1989 | European Pat. Off. . |
| 0329268 | 8/1989 | European Pat. Off. . |
| 3718326 | 12/1988 | Fed. Rep. of Germany . |
| 2220914 | 1/1990 | United Kingdom . |

*Primary Examiner*—Andres Kashnikow
*Assistant Examiner*—J. A. Kaufman
*Attorney, Agent, or Firm*—Gary L. Griswold; Walter N. Kirn; James D. Christoff

[57] ABSTRACT

An assembly for mixing and dispensing preparations such as dental cements includes a capsule and a lever actuated dispensing device. The capsule is received in a first orientation of the dispensing device for initial movement of a piston of the capsule to combine two components in a mixing chamber of the capsule. The capsule is received in a second orientation when dispensing of the components is desired. The capsule includes flanges engageable with one or more retention members of the dispensing device, and the flanges are positioned to substantially utilize the mechanical advantage provided by the dispensing device regardless of whether the capsule is in the first orientation or in the second orientation. The flanges are also arranged to substantially prohibit bursting of the capsule when the components are discharged from the mixing chamber, and essentially preclude dispensing of the components when the capsule is in the first orientation.

14 Claims, 4 Drawing Sheets

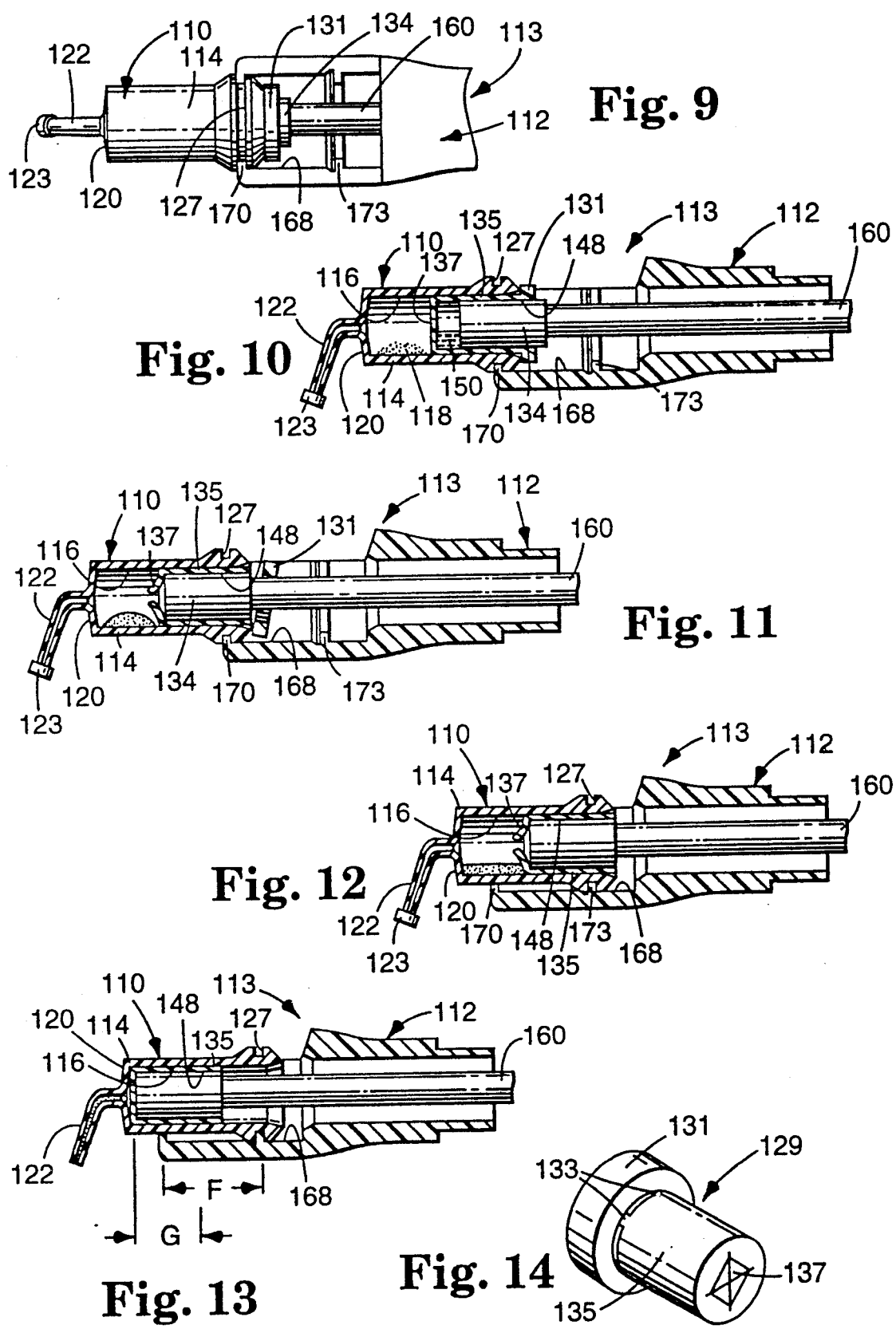

TWO-STAGE MIXING AND DISPENSING ASSEMBLY FOR PREPARATIONS SUCH AS DENTAL CEMENTS

This application is a continuation-in-part of application Ser. No. 07/735,995, filed Jul. 25, 1991 now abandoned.

BACKGROUND OF THE INVENTION

1. Field of the Invention

This invention relates to an assembly for mixing and dispensing preparations of two or more components.

2. Description of the Related Art

A number of devices have been developed which are intended to serve as a shipping, storage, mixing and dispensing container for small quantities of preparations made of two or more components. Some of these devices are particularly desirable for single-use applications such as one-patient applications in the medical and dental fields. Certain devices, for example, are used in dentistry for two-component glass ionomer cement systems that serve as adhesives, bases, liners, luting agents, sealants, and filling materials for restorative or endodontic use.

Ionomer cement systems typically are made by mixing a small quantity of glass powder with an aqueous solution of polycarboxylic acid. Representative ionomer cement systems are described in U.S. Pat. Nos. 4,872,936, 4,209,434 and 3,814,714 as well as European Patent Application Nos. 0 323 120 and 0 329 268. Dental ionomer cement systems are often characterized as having relatively short working times (e.g., on the order of one to two minutes) and as a consequence preferably are applied directly to the tooth cavity or other work site from a capsule or other small container that is used for both mixing and dispensing the cement.

Mixing and dispensing capsules for two-component dental preparations are described in U.S. Pat. Nos. 3,595,439 and 4,648,532 and U.K. Patent Application No. 2 220 914. In brief, such capsules include a hollow capsule body having an outlet on one end, a piston received in an opposite end, and a barrier within the body that initially separates the two components. When desired, the barrier is ruptured and the components are mixed by placing the capsule in an amalgamator. The capsule is then placed in a dispensing device to advance the piston and eject the mixed preparation through the outlet.

The barrier of the capsule described in U.S. Pat. No. 3,595,439 is ruptured by placing the capsule in a pressure-inducing device that together advances a cap and plunger toward a tubular body portion. After the components are mixed in an amalgamator, the capsule is placed in a receptacle of a hand extruder having a ram which is movable through a hole in the capsule cap for advancement of the plunger to dispense the preparation while the cap remains stationary.

Advantageously, the overall length of the capsule shown in U.S. Pat. No. 3,595,439 is too large to fit within the receptacle of the extruder unless the barrier has been ruptured by advancement of the cap and plunger toward the tubular body of the capsule. Such construction serves to remind the user that there are two components in the capsule that should be mixed by the amalgamator before beginning the dispensing operation.

However, the mixing and dispensing capsule described in U.S. Pat. No. 3,595,439 is used with two tools: the pressure-inducing device to rupture the barrier and "activate" the capsule, and the hand extruder for discharging the mixed preparation from the capsule. The purchase, handling and cleaning of two tools results in additional time and expense.

U.K. Patent Application No. 2 220 914 describes in one embodiment an assembly of a capsule and a single dispensing device, wherein the dispensing device is placed in a first position to rupture a barrier and then placed in a second position to eject the contents. However, there is a possibility that a ram of the dispensing device may be advanced too far when such a capsule is in its first position, resulting in unintentional discharge of the contents of the capsule before the contents have been properly mixed.

SUMMARY OF THE INVENTION

An assembly in accordance with the invention for mixing and dispensing a preparation comprises a capsule including a body having a chamber and a front end portion with outlet structure. The capsule includes a piston received in the chamber. The piston is movable in the chamber along a limited path of travel toward the front end portion. The capsule includes a barrier in the chamber. The assembly further includes a dispensing device including a housing having a receptacle with a reference axis. The receptacle includes structure for detachably receiving the capsule in either a first orientation or a second orientation spaced from the first orientation in a direction along the axis. The device includes a lever movably coupled to the housing and a ram connected to the lever. The ram is operable to move the piston in a direction along the axis when the capsule is received in the receptacle and the lever is moved relative to the housing.

When the capsule is received in the first orientation, the ram is operable to move the piston to a certain location wherein the barrier opens as the piston reaches the certain location. When the capsule is received in the second orientation, the ram is operable to move the piston to a certain position that is substantially the same as the forwardmost limit of the path of travel of the piston in the chamber. The first orientation is spaced from the second orientation a distance that is at least as great as the distance between the certain location and the certain position.

The barrier provides initial separation of a first component from a second component of the preparation. Preferably, the ram of the device reaches its limit of travel once the barrier is opened and the capsule is in the first orientation, in order to avoid undue reduction in the space available for mixing the components. Reaching the end of possible movement of the ram also provides tactile feedback to the user that the first stage of operation is essentially complete.

BRIEF DESCRIPTION OF THE DRAWINGS

FIG. 9 is a fragmentary, plan view of a capsule and a dispensing device in accordance with another embodiment of the invention;

FIG. 10 is a fragmentary, side cross-sectional view of the capsule and dispensing device illustrated in FIG. 9;

FIG. 11 is a view somewhat similar to FIG. 10 except that a ram of the dispensing device has been advanced to move a piston of the capsule to a certain location to open a barrier;

FIG. 12 is a view somewhat similar to FIG. 11 except that the capsule has been placed in a second orientation in the dispensing device and the ram has been retracted;

FIG. 13 is a view somewhat similar to FIG. 12 except that the ram has been advanced to move the piston forward and expel a preparation through outlet structure; and FIG. 14 is an enlarged perspective view of an inner cup of the capsule.

DETAILED DESCRIPTION OF THE PREFERRED EMBODIMENTS

Figure 1:
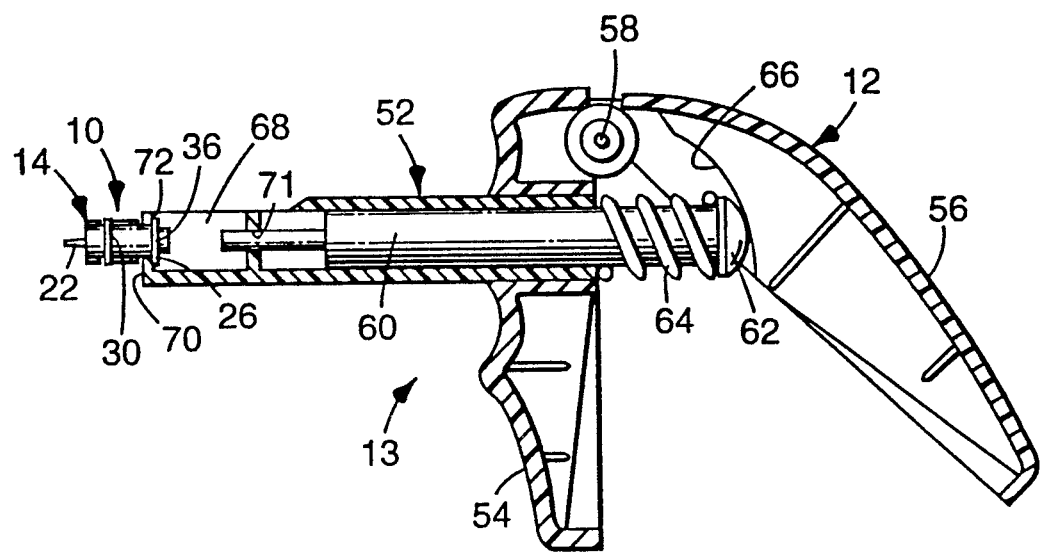
FIG. 1 is a side cross-sectional view of a capsule and a dispensing device in accordance with one embodiment of the invention.
Figure 2:
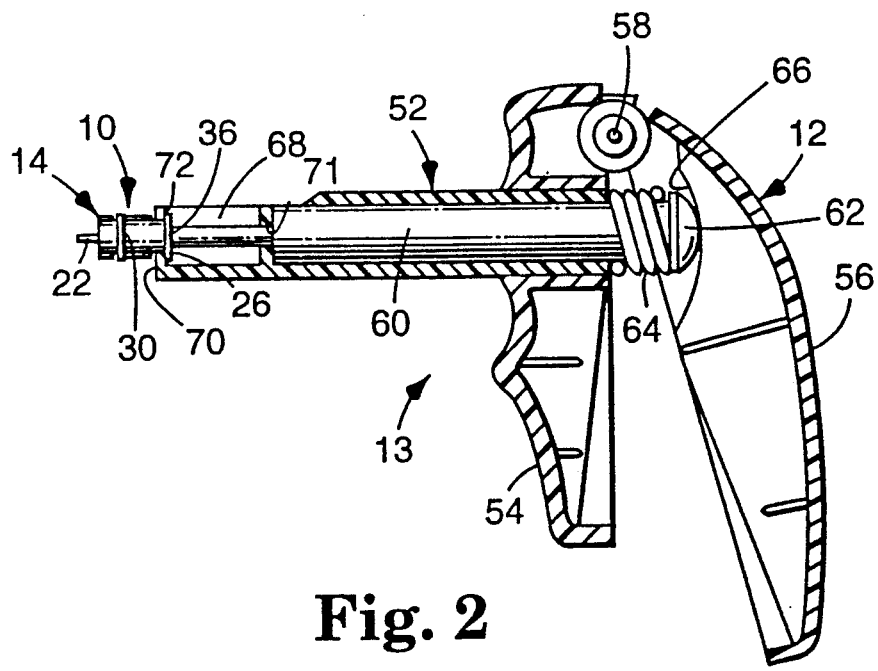
FIG. 2 is a view somewhat similar to FIG. 1 except that a lever of the dispensing device has been pivoted to advance a ram of the device to its limit of forward movement.

A capsule 10 for mixing and dispensing a preparation made of two or more components is shown in FIGS. 1–7. Preferably, the capsule is used in combination with a dispensing device 12 that is illustrated in FIGS. 1 and 2. The capsule 10 and the device 12 constitute a two-stage mixing and dispensing assembly 13.

Figure 3:
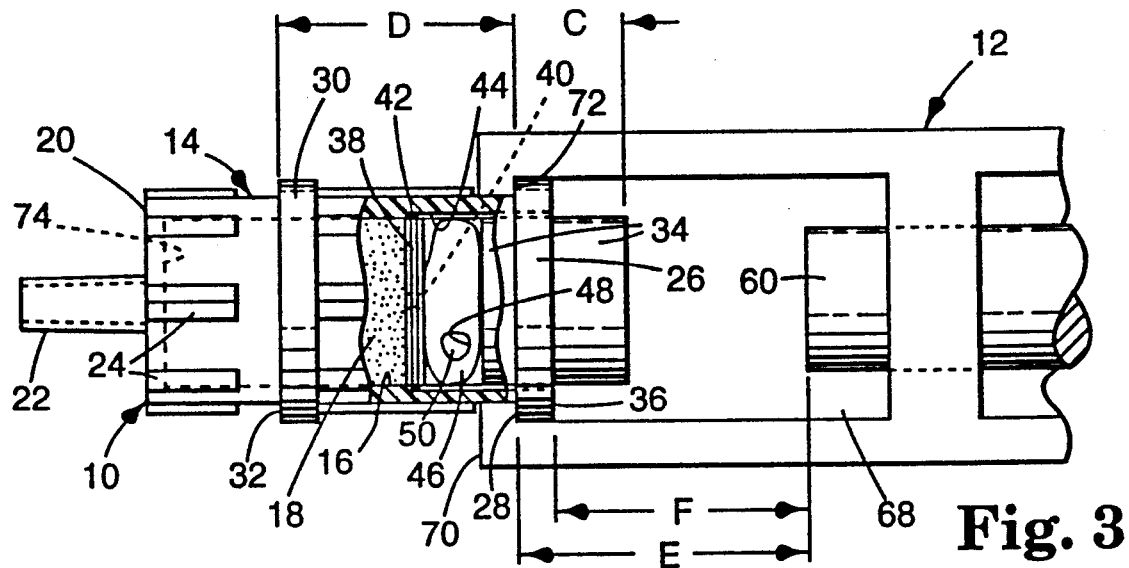
FIG. 3 is a fragmentary, enlarged top view of the capsule and dispensing device shown in FIG. 1.

As can be observed in, for example, FIG. 3, the capsule 10 includes a generally cylindrical, tubular body 14 having an internal, cylindrical chamber 16 that contains a first component 18 of the preparation. Additionally, the body 14 has a front end portion 20 with outlet structure 22 that comprises a projecting nozzle. Although not shown, the outlet structure 22 is initially covered by a cap, and has partial Luer-type threads for twist-on connection with a nozzle extension useful for reaching areas of the oral cavity that might otherwise be difficult to access.

Figure 7:
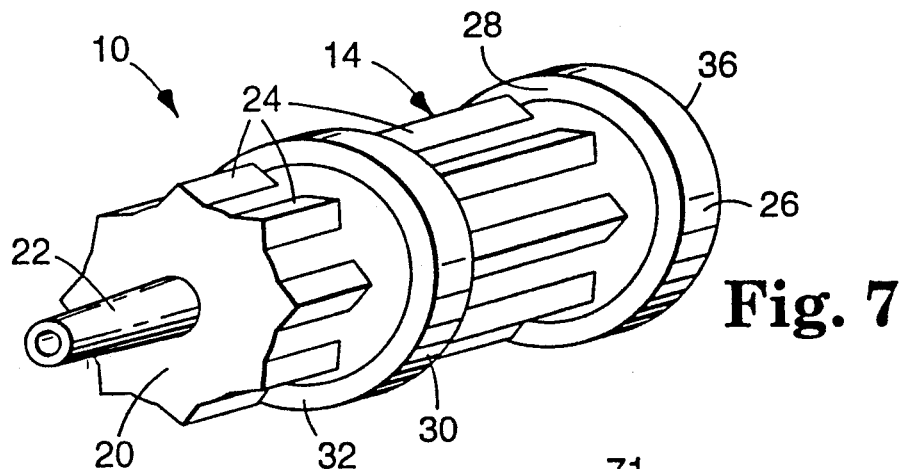
FIG. 7 is a perspective view of the capsule shown in FIGS. 1–6.

As shown for example in FIG. 7, the periphery of the body 14 is somewhat star-shaped, and presents a plurality of elongated, front-to-back ridges 24 for enhancing the user's grip on the capsule body 14 when turning the body 14 and/or the nozzle extension relative to the dispensing device 12.

The body 14 also includes a first peripheral, circumscribing flange 26 that extends radially outwardly from a longitudinal, central axis of the body 14. The first flange 26 has a first wall section 28 that faces the front end portion 20. The body has a second flange 30 that is similar to the first flange 26 and has a second wall section 32 that also faces the front end portion 20.

A cylindrical piston 34 is initially received in a rear end portion 36 of the body 14 as shown in FIG. 3, and has an outer diameter that is complemental and approximately equal to the inner diameter of the chamber 16. The piston 34 is movable in the chamber 16 along a path coincident with the central, longitudinal axis of the chamber 16 and the body 14.

A generally circular disc 38 is received in the chamber 16 and has a central opening 40 as well as four tabs 42 spaced equally around the periphery of the disc 38. When assembling the disc 38 and the body 14, the tabs 42 are guided along four mating slots 44 until reaching the front end of the latter. The disc 38 is similar to a disc of a two-component capsule of Ernst Muhlbauer KG (Hamburg, Germany).

As illustrated in FIG. 3, a barrier in the nature of a pouch or pillow 46 is made of a layered polyethylene and aluminum foil material. The pillow 46 is located between the disc 38 and the piston 34 and has an internal, initially closed compartment 48 that receives a second component 50 of the preparation.

The capsule 10 may be conveniently used to dispense dental ionomer cement systems such as the system described in the aforementioned European Patent Application No. 0 323 120. In such an instance, the first component 18 comprises a glass powder and the second component 50 comprises an aqueous solution of polycarboxylic acid. However, the capsule 10 is also useful for mixing and dispensing other preparations made of two or more components.

The dispensing device 12 is preferably used in combination with the capsule 10 and is similar to the device described in U.S. Pat. No. 4,198,756. The device 12 includes a housing 52 having a transverse grip 54 as shown in FIGS. 1 and 2. A rear lever 56 is connected to the grip 54 by a pivotal connection 58 for swinging movement between the positions shown in FIGS. 1 and 2.

The housing 52 includes a cylindrical channel that slidably receives a ram 60 having a necked-down, cylindrical front section with a flat front end. A rear end of the ram 60 has a somewhat semi-spherical, enlarged head 62, and a coiled compression spring 64 surrounding the ram 60 between the head 62 and the grip 54 urges the ram 60 in a rearward direction toward the lever 56.

A curved cam surface 66 is formed on the lever 56 and is in sliding engagement with the head 62. As the lever 56 is moved toward the grip 54 in arc about the pivotal connection from its orientation shown in FIG. 1 and to its orientation shown in FIG. 2 (as would occur when the hand of the user squeezes the lever 56 against the grip 54), the head 62 rides along the cam surface 66 and moves the ram 60 in a forward direction toward a front portion of the dispensing device 12. When the lever 56 is released, the spring 64 moves both the ram 60 and the lever 56 from the respective positions shown in FIG. 2 and to the positions shown in FIG. 1.

Figure 8:
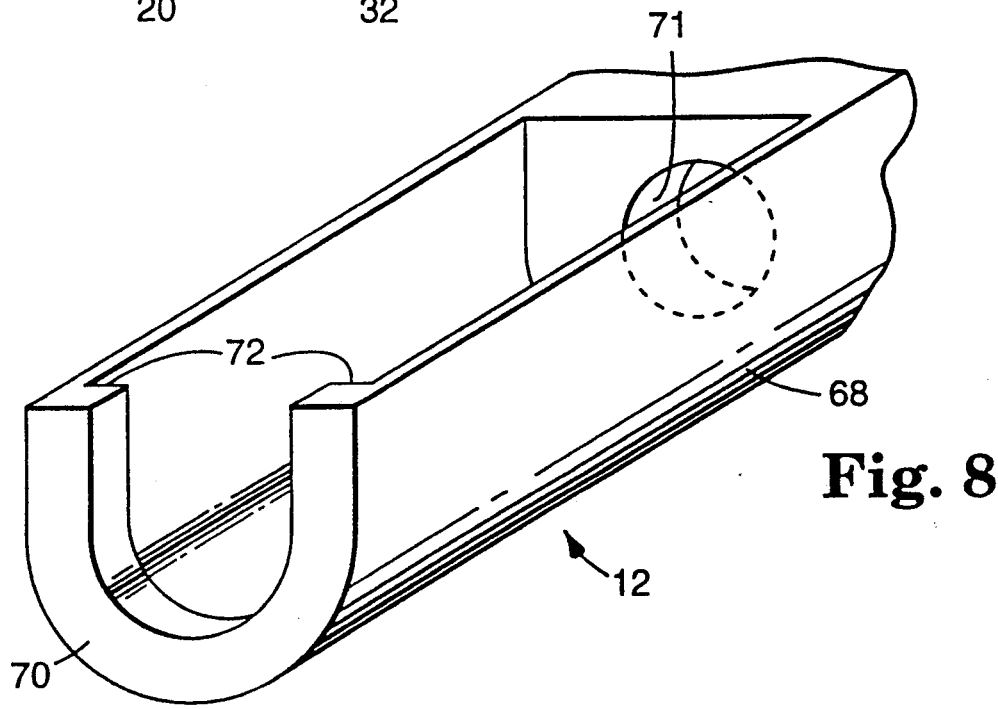
FIG. 8 is a fragmentary, perspective view of a front end portion of the dispensing device shown in FIGS. 1–6.

The front end portion of the dispensing device 12 includes a receptacle 68 having a longitudinal reference axis that is collinear with the central axis and the path of sliding movement of the ram 60 and its necked-down front portion. The receptacle 68 terminates at its front end by a generally U-shaped retention wall member 70 (see FIGS. 3–6 and 8) and at its rear end by a rear wall having a hole 71 (FIG. 8) for receiving the front necked-down section of the ram 60.

In use, the capsule 10 is initially placed in the receptacle 68 in a first orientation that is shown in FIGS. 1–4 wherein the first wall section 28 is in abutting contact with a rear-facing wall surface 72 of the retention member 70. Next, the lever 56 is moved in an arc about the pivotal connection 58 to advance the ram 60 and cause the front end of the ram 60 to engage the rear end of the piston 34. Continued movement of the lever 56 to its orientation shown in FIG. 2 shifts the ram 60 and the piston 34 therewith to the respective positions shown in FIG. 4.

Figure 4:
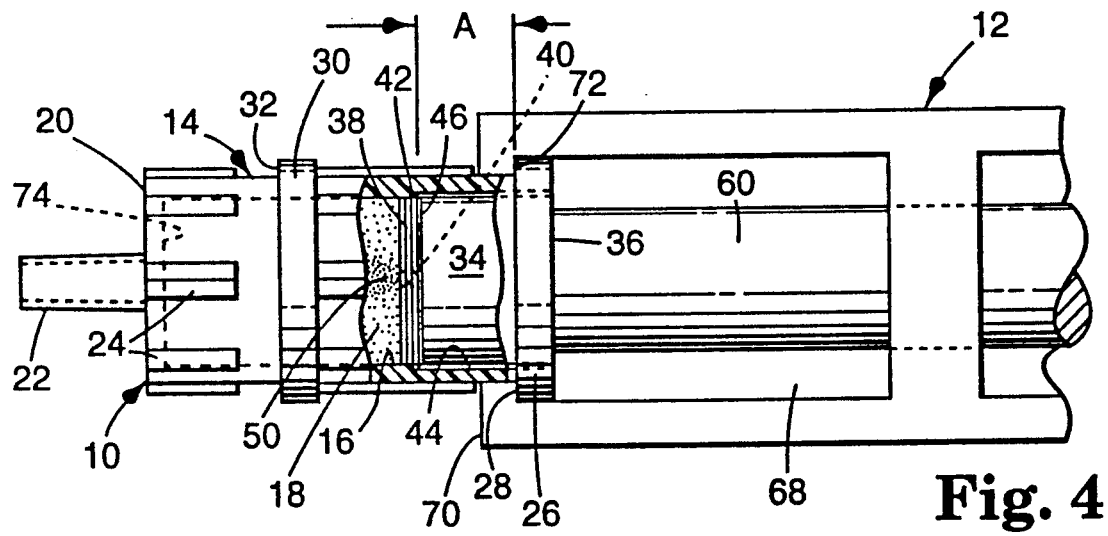
FIG. 4 is a fragmentary, enlarged top view of the capsule and dispensing device depicted in FIG. 2, showing a piston of the capsule moved forward to expel a second component of a preparation into a chamber that contains a first component.

As the piston 34 is moved from its initial position shown in FIG. 3 and to its intermediate position shown in FIG. 4, the pillow 46 is compressed against the disc 38, causing the pillow 46 to rupture and open. Continued movement of the piston 34 to its position shown in FIG. 4 compresses the pillow 46 against the disc 38, and causes the second component 50 to be expelled from the compartment 48 and discharged into the chamber 16 through the opening 40. As can be appreciated, the disc 38 serves as a means to open the barrier or pillow 46, discharge the second component 50 from the compartment 48, and bring the second component 50 into substantial contact with the first component 18 when the piston 34 is moved to the position shown in FIG. 4. As the piston 34 continues to advance toward the front end portion 20 and flatten the pillow 46 against the disc 38, the disc 38 breaks away from the tabs 42 and advances from its position shown in FIG. 3 to its position shown in FIG. 4. The severed tabs 42 remain in the slots 44.

The ram 60 has an overall, limited extent of forward movement that is determined by the position of the ram 60 when the spring 64 is fully compressed as shown in FIG. 2. When the ram 60 has reached its forward limit of travel, the rear face of the piston 34 is flush with the rear surface of the first flange 26 and the disc 38 is in the position shown in FIG. 4 with the tabs 42 severed and the second component 50 substantially fully expelled into the chamber 16. Such construction ensures that the user cannot continue to advance the ram 60 and prematurely dispense the first component 18 and the second component 50 from the chamber 16 through the outlet structure 22.

Next, the capsule 10 is removed from the receptacle 60 and placed in an amalgamator. The amalgamator is activated for a sufficient amount of time to thoroughly mix the first component 18 and the second component 50 in the chamber 16 to form a preparation.

Figure 5:
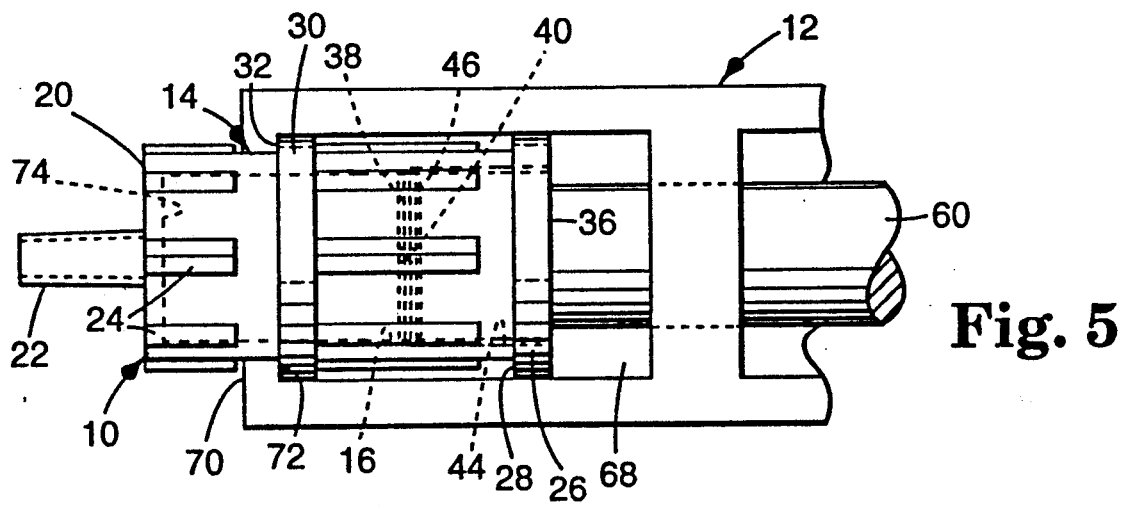
FIG. 5 is a view somewhat similar to FIG. 3 except that the capsule has been moved to a second orientation in a receptacle of the dispensing device.
Figure 6:
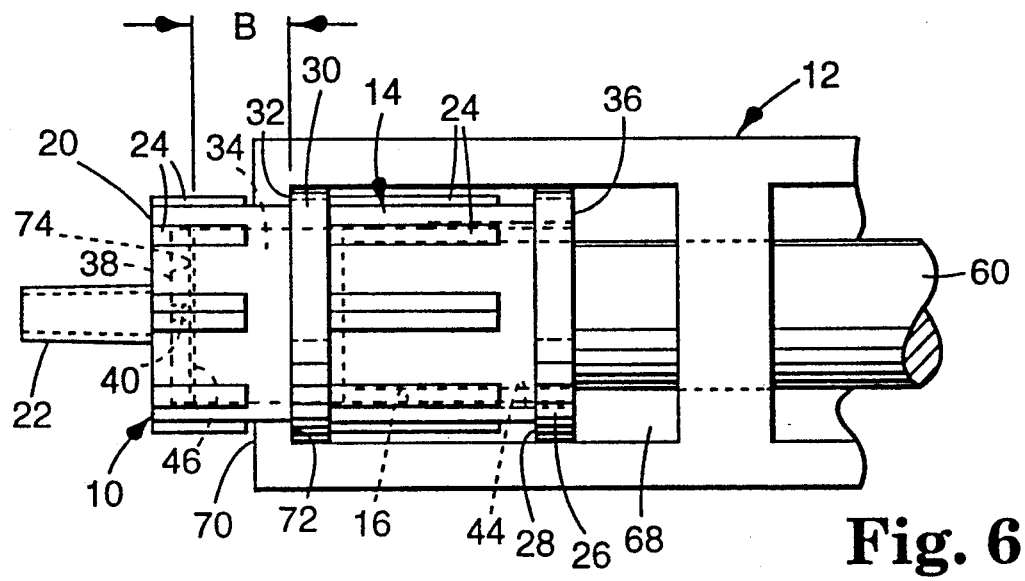
FIG. 6 is a view somewhat similar to FIG. 5 except that the ram of the dispensing device has been advanced to move a piston of the capsule forward in the chamber and expel a preparation from the chamber.

The capsule 10 is then returned to the receptacle 68, but in this instance is placed in a second orientation that is illustrated in FIGS. 5 and 6 wherein the second wall section 32 of the second flange 30 is in abutting contact with the rear surface 72 of the retention member 70. It should be noted, however, that if the user accidentally returns the capsule 10 to the first orientation (as shown in FIGS. 1–4), the user will soon realize that the capsule is in the wrong orientation for dispensing since the ram 60 will be unable to advance the piston 34 past its position shown in FIG. 4 and discharge of the preparation will not occur. As can be appreciated, the wall sections 28, 32 together with the retention member 70 comprise structure for detachably receiving the capsule 10 in either a first orientation or a second orientation spaced from the first orientation in a direction along the longitudinal reference axis of the receptacle 68.

Once the capsule 10 is in its second orientation as depicted in FIGS. 5 and 6, the lever 56 is pivoted toward the grip 54 to advance the ram 60 and move the piston 34 from its position shown in FIG. 5 and toward its position shown in FIG. 6. During such movement, the disc 38 and the pillow 46 are moved with the piston 34 toward the front end portion 20, and as the chamber 16 is reduced in volume the mixed preparation is extruded through the outlet structure 22, preferably directly to an application site such as a tooth cavity.

As the ram 60 is moved by the lever 56 to its forwardmost allowable position, the piston 34 is advanced toward the front end portion 20 to a position wherein a front surface of the disc 38 is in firm, face-to-face contact with a flat, rear facing annular wall 74 of the chamber 16. As a result, substantially all of the preparation is expelled from the chamber 16 when the ram 60 and the piston 34 reach their forward limits of travel. Further, forward movement of the ram 60 is restricted by the fully compressed spring 64 so that the piston 34 and disc 38 do not burst through the front end portion 20 of the capsule 10.

When the ram 60 is in its forwardmost position and the capsule 10 is in its first orientation as shown in FIG. 4, the piston 34, and particularly the front end of the piston 34, is located a certain dimension that is marked A in FIG. 4 from the first wall section 28 of the first flange 26. When the capsule 10 is in its second orientation and the ram 60 is advanced to its forwardmost position (that is shown in FIG. 6), the front end of the piston 34 is located a dimension marked B in FIG. 6 from the second wall section 32 of the second flange 30. Advantageously, dimension A is equal to dimension B, so that in either instance the ram 60 travels along the same limited path of travel, and the entire extent of the mechanical advantage offered by the lever 56 is utilized. (Dimensions A and B could be taken from a portion of the piston other than its front end so long as the same portion was used for each measurement.)

Rearward movement of the ram 60 is normally limited by detents formed in the pivotal connection 58 such that, in normal use, the front end of the ram 60 retracts only to its position shown in FIGS. 1, 3 and 5. Consequently, the effective length of the receptacle 68 for reception of the capsule 10 is limited by the distance E (see FIG. 3) between the front end of the ram 60 and the rearwardly facing surface 72 of the retention member 70.

In addition, as can be observed in FIG. 3, the rear end of the piston 34 initially projects a certain distance marked C in FIG. 3 from the first wall section 28 of the first flange 26. Also, the first wall section 28 is spaced from the second wall section 32 by a dimension D (see FIG. 3). The sum of dimensions C and D is greater than the dimension E (measured between the surface 72 and the front end of the ram 60 when in its rearwardmost position) in order to prevent the capsule 10 from being placed in its second orientation until such time as the piston 34 has been advanced. Preferably, the dimension E is only slightly greater than the sum of dimension D and the thickness of the first flange 26 to ensure that the piston 34 has moved to its orientation shown in FIG. 4 with the contents of the compartment 48 fully expelled and the tabs 42 severed from remaining portions of the disc 38.

The overall limited movement of the ram 60 is not greater than dimension E regardless of whether the capsule 10 is in its first orientation or its second orientation in order to provide a relatively compact arrangement and still utilize in either instance the substantial mechanical advantage provided by the lever 56. As an alternative, the dimension A may be greater than the dimension B if desired.

The foregoing assembly 13 ensures that the user removes the capsule 10 from the receptacle 68 after the pillow 46 is ruptured. As a result, the user is reminded to place the capsule in an amalgamator to thoroughly mix the components 18, 50 and avoid discharging the components 18, 50 through the outlet structure 22 before thorough mixing in an amalgamator has occurred.

Fracture of the tabs 42 from the remaining portions of the disc 38 when the capsule 10 is in the first orientation provides tactile as well as audible feedback to the user that the proper position of the piston 34 has been reached and that the second component 50 is substantially discharged from the compartment 48.

Further, if desired, the tolerance between the piston 34 and the chamber 16 may be selected to allow the user to shift the piston 34 to its position shown in FIG. 4 by using the thumb rather than the dispensing device 12.

An assembly 113 according to a second, currently preferred embodiment of the invention is shown in FIGS. 9-13. The assembly 113 includes a capsule 110 and a dispensing device 112. The device 112 is substantially similar to the device 12 except for a front portion of the device 112 that is adjacent a receptacle 168 for receiving the capsule 110.

The capsule 110 includes a cylindrical, tubular polyethylene body 114 having an inner chamber 116. A first component 118 (FIG. 10) of a preparation is received in a front end portion 120 of the capsule 110 next to curved outlet structure 122 having a removable plug 123 with a tail that initially extends to the forward end of the chamber 116.

A rear portion of the capsule body 114 is circumscribed by two spaced apart flanges. The flanges present a pair of spaced apart wall sections that define a peripheral groove 127 having a U-shaped configuration in cross-section. A polyethylene cup 129 (illustrated alone in FIG. 14) is received in the rear portion of the chamber 116. The cup 129 includes a rear ring 131 that is initially connected in integral fashion at spaced apart locations by tabs 133 to a central cup section 135 that defines a compartment 148 (FIG. 10) for receiving a second component 150 of a dental preparation.

A frangible forward wall or barrier 137 of the cup 129 is provided with lines of weakness 139 (FIG. 14) having a pattern of a square with somewhat weaker (i.e., more pronounced) lines extending along both diagonals of the square. A cylindrical piston 134 is received in the compartment 148 and has a rear section that initially projects outwardly from the capsule 110 as illustrated in FIGS. 9-10.

In use, the capsule 110 is initially placed in a first orientation that is shown in FIGS. 9-11, wherein the groove 127 receives a first, forward, generally U-shaped retention member 170 of the device 112. A lever of the device 112 is then moved to advance a longitudinally movable ram 160 to a position as depicted in FIGS. 9-10 wherein the forward end of the ram 160 contacts the rear end of the piston 134.

Additional movement of the ram 160 shifts the piston 134 forwardly until the pressure within the compartment 148 causes the lines of weakness of the barrier 137 to rupture. The barrier opens in petal-like fashion and, once opened, enables passage of the second component 150 into the chamber 116.

Continued advancement of the ram 60 causes the front end of the piston 134 to bear against remaining outer, unruptured regions of the barrier 137 and causes the cup section 135 along with the barrier 137 to advance toward the outlet structure 122. As the cup section 135 advances, the tabs 133 break, detaching the ring 131 from the cup section 135.

The lines of weakness of the barrier 137 are constructed to open under the influence of pressure within the compartment 148 of a value that is less than the pressure needed to fracture the tabs 133. As a result, the second component 150 is discharged from the compartment 148 before the ring 131 detaches from the cup section 135. Breakage of the tabs 133 provides both visual and tactile feedback to the user that the capsule 110 has been "activated" by bringing the second component 150 into contact with the first component 118.

Further, the ram 160 reaches its forwardmost limit of travel (as depicted in FIG. 11) once the barrier 137 opens and the tabs 133 fracture. As a consequence, sufficient space is available in the chamber 116 for mixing the first component 118 with the second component 150 and undue reduction in the space is avoided. The forwardmost limit of movement of the ram 160 also essentially prevents dispensing of the components 118, 150 through the outlet structure 122 when the capsule 110 is in the first orientation, so that dispensing of an unmixed preparation is not likely to occur.

Next, the capsule 110 and the ring 131 are removed from the receptacle 168. The capsule 110 is placed in an amalgamator and the amalgamator is activated for a sufficient amount of time to thoroughly mix the components 118, 150 in the chamber 116 to form a preparation. Subsequently, the capsule 110 is returned to the receptacle 168 in a second orientation as shown in FIGS. 12 and 13 wherein the groove 127 engages a second generally U-shaped retention member 173 of the device 112.

Next, the plug 123 is removed from the outlet structure 122. The lever of the device 112 is then moved to advance the ram 160 and thereby shift the piston 134 from its position as shown in FIG. 12 and toward its position as shown in FIG. 13, causing the preparation to be dispensed through the outlet structure 122.

To ease use, the handles of the dispensing device are not fully closed (i.e., are not adjacent one another) when the ram 160 reaches the end of its necessary path of travel to advance the piston 134 to the position shown in FIG. 11 when the capsule 110 is in its first orientation, or to the position shown in FIG. 13 when the capsule 110 is in its second orientation. Preferably, one of the handles has a protrusion that contacts the other handle and precludes further closing of the handles if an attempt is made to advance the ram 160 past the position shown in FIG. 11.

The first orientation of the capsule 110 in the receptacle 168 is spaced from the second orientation of the capsule 110 by a distance represented by the letter F in FIG. 13 (for exemplary purposes, the location of each orientation is determined by the location of the groove 127 when the capsule 110 is placed in either orientation). The letter G in FIG. 13 represents the dimension of the distance between the certain location of the piston 134 as shown in FIG. 11 and the certain position of the piston 134 as shown in FIG. 13 (as determined for exemplary purposes from the forward end of the piston 134). The dimension F is equal, or at least as great as the dimension G so that (1) the space available in the chamber 116 for mixing the components 118, 150 after the barrier 137 is ruptured is not unintentionally reduced, and (2) dispensing of the components 118, 150 is essentially precluded when the capsule 110 is in the first orientation.

I claim:

1. An assembly for mixing and dispensing a preparation comprising:

a capsule including a body having a chamber and a front end portion with outlet structure, said capsule including a piston received in said chamber, said piston being movable in said chamber along a limited path of travel toward said front end portion, said capsule including a barrier in said chamber; and a dispensing device including a housing having a receptacle with a reference axis, said receptacle including structure for detachably receiving said capsule in either a first orientation or a second orientation spaced from said first orientation in a direction along said axis, said device including a lever movably coupled to said housing and a ram connected to said lever, said ram being operable to move said piston in a direction along said axis when said capsule is received in said receptacle and said lever is moved relative to said housing, said ram when said capsule is received in said first orientation being operable to move said piston to a certain location wherein said barrier opens as said piston reaches said certain location, said ram when said capsule is received in said second orientation being operable to move said piston to a certain position that is substantially the same as the forwardmost limit of the path of travel of said piston in said chamber, said first orientation being spaced from said second orientation a distance that is at least as great as the distance between said certain location and said certain position.

2. The assembly of claim 1, wherein said structure for detachably receiving said capsule comprises a first retention member and a second retention member spaced from said first retention member in a direction along said axis.

3. The assembly of claim 1, wherein said structure for detachably receiving said capsule comprises a sole generally U-shaped retention member.

4. The assembly of claim 1, wherein said barrier comprises a rupturable pillow.

5. The assembly of claim 1, wherein said barrier comprises a frangible wall.

6. An assembly for mixing and dispensing a preparation comprising:

a capsule including a body having a chamber and a front end portion with outlet structure, said capsule including a piston received in said chamber, said piston being movable in said chamber along a limited path of travel toward said front end portion, said capsule including a barrier in said chamber; and a dispensing device including a housing having a receptacle with a reference axis, said receptacle including structure for detachably receiving said capsule in either a first orientation or a second orientation spaced from said first orientation in a direction along said axis, said device including a lever movably coupled to said housing and a ram connected to said lever, said ram being operable to move said piston in a direction along said axis when said capsule is received in said receptacle and said lever is moved relative to said housing, said ram when said capsule is received in said first orientation being operable to move said piston to a certain location wherein said barrier opens as said piston reaches said certain location, said ram when said capsule is received in said second orientation being operable to move said piston to a certain position that is substantially the same as the forwardmost limit of the path of travel of said piston in said chamber, said first orientation being spaced from said second orientation a distance that is generally equal to the distance between said certain location and said certain position.

7. The assembly of claim 6, wherein said structure for detachably receiving said capsule comprises a first retention member and a second retention member spaced from said first retention member in a direction along said axis.

8. The assembly of claim 6, wherein said structure for detachably receiving said capsule comprises a sole generally U-shaped retention member.

9. The assembly of claim 6, wherein said ram has an overall, limited extent of forward movement when said capsule is received in said receptacle that is substantially the same regardless of whether said capsule is in said first orientation or in said second orientation.

10. The assembly of claim 6, wherein said body has a longitudinal axis and is somewhat star-shaped in transverse section.

11. An assembly for mixing and dispensing a preparation comprising:

a capsule including a body having a chamber and a front end portion with outlet structure, said capsule including a piston received in said chamber, said piston being movable in said chamber along a limited path of travel toward said front end portion, said capsule including a barrier in said chamber; and a dispensing device including a housing having a receptacle with a reference axis, said receptacle including structure for detachably receiving said capsule in either a first orientation or a second orientation spaced from said first orientation in a direction along said axis, said device including a lever movably coupled to said housing and a ram connected to said lever, said ram being operable to move said piston in a direction along said axis when said capsule is received in said receptacle and said lever is moved relative to said housing, said ram when said capsule is received in said first orientation being operable to move said piston to a certain location wherein said barrier opens as said piston reaches said certain location, said ram when said capsule is received in said second orientation being operable to move said piston to a certain position that is substantially the same as the forwardmost limit of the path of travel of said piston in said chamber, said ram having an overall, limited extent of forward movement as determined when said capsule is not received in said receptacle, said limited extent being a dimension that is approximately equal to the distance that said first orientation is spaced from said second orientation.

12. An assembly for mixing and dispensing a preparation comprising:

a capsule including a body having a chamber for receiving a first component of a preparation, said body including a front end portion with outlet structure, said capsule including a piston received in said chamber, said piston being movable in said chamber along a limited path of travel toward said front end portion, said capsule including a compartment for receiving a second component of the preparation and means for discharging the second component into said chamber as said piston reaches a certain location along its path of travel; and a dispensing device including a housing having a receptacle with a reference axis, said receptacle including structure for detachably receiving said capsule in either a first orientation or a second orientation spaced from said first orientation in a direction along said axis, said device including a lever movably coupled to said housing and a ram connected to said lever, said ram being operable to move said piston in a direction along said axis when said capsule is received in said receptacle and said lever is moved relative to said housing, said ram when said capsule is received in said first orientation being operable to move said piston to said certain location, said ram when said capsule is received in said second orientation being operable to move said piston to a certain position that is substantially the same as the forwardmost limit of the path of travel of said piston in said chamber, said first orientation being spaced from said second orientation a distance that is at least as great as the distance between said certain location and said certain position.

13. The assembly of claim 12, wherein said means comprises a frangible wall.

14. The assembly of claim 12, wherein said means comprises a rupturable pillow.

* * * * *